United States Patent
Li et al.

(10) Patent No.: US 11,160,820 B2
(45) Date of Patent: Nov. 2, 2021

(54) PHARMACEUTICAL USE OF ARGININYL FRUCTOSY GLUCOSE

(71) Applicant: Dalian Minzu University, Dalian (CN)

(72) Inventors: Keke Li, Dalian (CN); Xiaojie Gong, Dalian (CN)

(73) Assignee: Dalian Minzu University, Dalian (CN)

( * ) Notice: Subject to any disclaimer, the term of this patent is extended or adjusted under 35 U.S.C. 154(b) by 0 days.

(21) Appl. No.: 16/898,123

(22) Filed: Jun. 10, 2020

(65) Prior Publication Data
US 2020/0376016 A1   Dec. 3, 2020

(30) Foreign Application Priority Data
May 30, 2019   (CN) .......................... 201910461647.7

(51) Int. Cl.
  *A61K 31/7028*   (2006.01)
  *A61P 1/16*   (2006.01)
(52) U.S. Cl.
  CPC ............ *A61K 31/7028* (2013.01); *A61P 1/16* (2018.01)
(58) Field of Classification Search
  None
  See application file for complete search history.

(56) References Cited

FOREIGN PATENT DOCUMENTS

| | | | | |
|---|---|---|---|---|
| CN | 104257672 A | * | 1/2015 | ......... A61K 31/7016 |
| KR | 10-2013-0002542 | * | 7/2014 | ........... A61K 36/258 |

OTHER PUBLICATIONS

Nam, Y., Bae, J., Jeong, J. H., Ko, S. K., & Sohn, U. D. (2018). Protective effect of ultrasonication-processed ginseng berry extract on the D-galactosamine/lipopolysaccharide-induced liver injury model in rats. Journal of ginseng research, 42(4), 540-548. (Year: 2018).*

* cited by examiner

*Primary Examiner* — Dale R Miller
(74) *Attorney, Agent, or Firm* — Enshan Hong; MagStone Law, LLP

(57) ABSTRACT

The present invention discloses a pharmaceutical use of argininyl fructosy glucose (AFG), and belongs to the field of research and development of pharmaceutical products. The pharmaceutical use refers to application of the AFG as an active ingredient in preparation of a drug for treating or preventing an acute hepatic failure disease (AHFD). The AHFD is an oxidative stress injury caused by use of a combination of lipopolysaccharide (LPS) and D-galactosamine (D-GalN), and the drug is used for protecting liver cells from injuries, and reducing apoptosis caused by LPS/D-GalN. The purity of the AFG is 80%-99.99%. The present invention proposes the use of the AFG in prevention or treatment of the acute hepatic failure for the first time, which provides a new raw material for the preparation of the drug for the acute hepatic failure, and also provides a new method for the prevention and treatment of the acute liver failure.

11 Claims, 1 Drawing Sheet

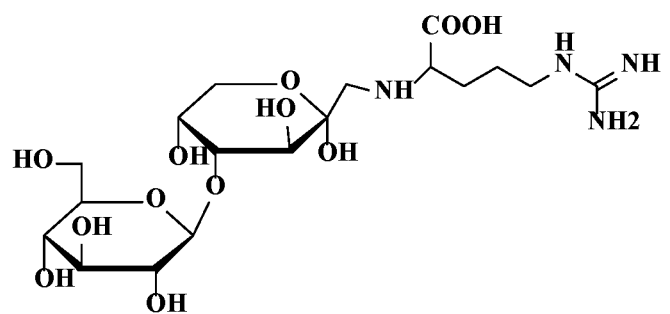

PHARMACEUTICAL USE OF ARGININYL FRUCTOSY GLUCOSE

CROSS-REFERENCE TO RELATED APPLICATIONS

This application claims priority to CN Pat. App. No. 201910461647. 7 entitled "PHARMACEUTICAL USE OF ARGININY FRUCTOSY GLUCOSE, which was filed on ay 30, 2019.

TECHNICAL FIELD

The present invention discloses a pharmaceutical use of argininyl fructosy glucose, and belongs to the medicine technology field of new biological activities of traditional Chinese medicine monomer compounds.

BACKGROUND

LPS refers to lipopolysaccharide, one of the components of a cell wall of a Gram-negative bacterium, which can induce many diseases and cause endotoxic shock, inflammatory diseases and multi-organ injures, and is related to the occurrence of tumor diseases. However, the LPS has low specificity for hepatic injuries when used alone. D-GalN refers to D-galactosamine, a phospho-uridine interferent for a hepatic cell, which can cause metabolic disorders, and induce inflammation and hepatic diffuse necrosis, and can cause fulminant hepatic failure when used in large doses. The use of a combination (LPS/D-GalN) of the lipopolysaccharide and the D-galactosamine can increase the specificity of the LPS for hepatic injuries, resulting in severe hepatitis. This model simulates the fulminant hepatic failure of human. The study of this model facilitates the intensive study of the process of clinical acute hepatic failure, and inflammation-mediated hepatic cell injuries and apoptosis of hepatic cells. At present, overuse of drugs and intake of toxic substances can cause a series of hepatic diseases. The acute hepatic failure is a special clinical syndrome, which causes a series of syndromes, including metabolic disorders, jaundice, coagulation disorders and neurological complications. The occurrence of this disease can lead to a higher mortality rate. At present, the more effective therapeutic regime is hepatic transplantation. Therefore, finding a drug for treating or improving the acute hepatic failure is of great significance.

Traditional Chinese medicines and active ingredients of traditional Chinese medicine extracts have certain therapeutic effects on acute hepatic injuries. Saponins are the main active ingredient in ginseng. There are many kinds of such an ingredient. Therefore, the action of the pharmacological activities of saponins have been extensively studied. For example, studies have confirmed that the ginsenoside Rg1 plays a protective role on mice with acute hepatitis/hepatic failure caused by LPS/D-GalN, through a TLR4 signaling pathway (International Immunopharmacology, 2018, 61:266-276.). However, few studies have been conducted on the action of the pharmacological activities of non-saponin ingredients in ginseng on liver.

SUMMARY

The present invention provides a pharmaceutical use of argininyl fructosy glucose, and proposes the use of the argininyl fructosy glucose (AFG) in prevention or treatment of acute hepatic failure for the first time, which provides a new raw material for the preparation of a drug for the acute hepatic failure, and also provides a new method for the prevention and treatment of the acute liver failure.

The aforementioned objective of the present invention is achieved by the following technical solution: a pharmaceutical use of argininyl fructosy glucose, which refers to application of the argininyl fructosy glucose as an active ingredient in preparation of a drug for treating or preventing an acute hepatic failure disease.

Further, the acute hepatic failure disease is an oxidative stress injury caused by use of a combination of lipopolysaccharide (LPS) and D-galactosamine (D-GalN), and the drug is used for protecting liver cells from injuries, and reducing apoptosis caused by LPS/D-GalN.

Further, the purity of the argininyl fructosy glucose is 80%-99.99%.

Further, the argininyl fructosy glucose, which is used as the only active ingredient, is mixed with an auxiliary ingredient or an additive ingredient to prepare to any dosage form of a drug for treating or preventing the acute hepatic failure disease.

Further, a combination of the argininyl fructosy glucose and other drugs is used as an active ingredient, and mixed with an auxiliary ingredient or an additive to a component to prepare any dosage form of a drug for treating or preventing the acute hepatic failure disease.

Further, a combination of the argininyl fructosy glucose and other drugs is used as an active ingredient, and mixed with an auxiliary ingredient or an additive ingredient to prepare any dosage form of a drug for treating or preventing the acute hepatic failure disease.

The AFG described in the present invention is safe for both oral and parenteral administration when used for the above uses. In case of oral administration, it can be administered in any conventional form, such as powder, tablets, pills, granules, capsules, solutions, injections, powder injections, patches, etc.

The drug for protecting from the acute hepatic failure prepared by the present invention is composed of the AFG as the only active monomer or active ingredient and a solid or liquid excipient, and the solid or liquid excipient used herein is well known in the art, and the follow are a few examples of them. Granules can be directly swallowed, or drunk by dissolving in water. The added auxiliary materials such as starch, sucrose, lactose, cellulose derivatives and the like promote better kneading and easy granulation of the drug. Tablets can be used for oral administration, and can be added with starch, pregelatinized starch, dextrin, sucrose, lactose, microcrystalline celluloses, mannitol, calcium sulfate, calcium hydrogen phosphate, calcium carbonate, light magnesium oxide and the like as diluents of the drugs, and added with purified water as wetting agents of the drugs; added with starch pulp, methyl celluloses, hydroxypropyl celluloses, hydroxypropyl methylcelluloses, sodium carboxymethyl celluloses, ethyl celluloses, povidone, syrup, mucilage, polyethylene glycol and the like as adhesives of the drugs; added with dry starch, sodium carboxymethyl starch, low substituted hydroxypropyl celluloses, cross-linked sodium carboxymethyl celluloses, cross-linked povidone, effervescent disintegrants and the like as disintegrants of the drugs; added with stearic acid, magnesium stearate, calcium stearate, talcum powder, micro silica gel, hydrogenated vegetable oil, polyethylene glycol and magnesium lauryl sulfate as lubricants of the drugs; and at the same time can be added with colorants such as natural pigments and synthetic dyes to improve the appearance and facilitate identification, and also can be added with aromatic agents and sweeteners.

The AFG described in the present invention is mixed with the aforementioned different auxiliary materials to prepare different products such as drugs, health care products or foods.

The argininyl fructosy glucose (AFG), has a molecular formula of $C_{18}H_{34}N_4O_{12}$, a chemical structural formula as shown in FIG. 1, and a relative molecular mass of 498.48, and is white powder that is presented purplish red in a ninhydrin reaction, soluble in water, and insoluble in organic solvents such as methanol and n-butanol. The AFG exists in red ginseng, and is a product of a Maillard reaction during processing the ginseng into the red ginseng.

Up to now, the AFG has not been involved in any research on hepatic injuries. The present invention creatively puts forward the effect of the AFG against the acute hepatic failure and confirms the effect by means of relevant experiments.

The present invention has the following beneficial effects.

(1) The AFG is used in preparation of a drug against the acute hepatic failure for the first time, which provides a brand-new drug raw material and means; and the AFG is an effective liver protective agent which can protect liver cells, reduce drug-induced apoptosis and weaken oxidative stress.

(2) The AFG against the acute hepatic injuries used by the present invention is derived from red ginseng, is a monomer compound of traditional Chinese medicine, and has mature processes such as extraction and synthesis processes, so that the AFG has abundant sources and has potential medical values and good social benefits in preparation of a product for preventing and treating the acute hepatic failure diseases. Furthermore, this compound has no obvious toxic and side effects when taken orally, and thus has better safety.

BRIEF DESCRIPTION OF THE DRAWINGS

FIG. 1 shows a chemical structural formula of argininyl fructosy glucose (AFG).

DESCRIPTION OF THE EMBODIMENTS

The technical solution of the present invention will be further described below with reference to specific examples, but the present invention is not limited to the contents of the examples in any form. The test methods described in the examples are conventional methods, unless otherwise specified. Unless otherwise specified, both the reagents and biomaterials are commercially available.

Preferably, argininyl fructosy glucose with a purity greater than 98.5% (HPLC); lipopolysaccharide (LPS) with a purity greater than 99%; and D-galactosamine (D-GalN) with a purity greater than 99%, are available from Solarbio, China.

All of alanine transaminase (ALT), Aspartate transferase (AST), Malondialdehyde (MDA), Catalase (CAT), glutathione (GSH) and superoxide dismutase (SOD) are purchased from Nanjing Jiancheng Bioengineering Institute; both of the RIPA lysis buffer and PMSF are purchased from Beyotime Biotechnology, China; the TUNEL kit is purchased from TransGen Biotech, Beijing.

The ST-16R high speed centrifuge is available from Thermo Fisher Scientific, USA; the JEM-2 000EX transmission electron microscope is available from Japan Electron Optics Laboratory Co., Ltd.; the IKART-10 tissue disperser is available from IKA (Germany); the HH-ZK1 single-hole intelligent water bath pot is available from Gongyi Yuhua Instrument Co. ltd.; the GL-88B vortex mixer is available from Haimen Kylin-Bell Lab Instruments Co., Ltd.; the Multiskan Ascent microplate reader is available from Thermo, USA; and the Enspire2 300PE multi-function microplate reader is available from Perkin Elmer, USA.

Example 1 Preparation of Drug

Preparation of capsules: 100 g of the argininyl fructosy glucose was added with and uniformly mixed with appropriate amount of starch and lactose in a manner of increment by equal quantity, then filled into capsules after passing the inspection, and packaged to obtain the finished product. 400 capsules were prepared, each containing 250 mg of the argininyl fructosy glucose.

Example 2 Preparation of Drug

Preparation of tablets: 100 g of the argininyl fructosy glucose was added with appropriate amount of starch and 1.5 g of magnesium stearate, fully mixed, and tableted to obtain the product. Each tablet weighed 0.3 g and contained 250 mg of the argininyl fructosy glucose.

Example 3 Preparation of Drug

Preparation of immediate-release pellets: 3 parts of the argininyl fructosy glucose is mixed with 7 parts of the microcrystalline cellulose evenly, added with 7 parts of 70% ethanol, kneaded continuously to prepare a soft material, extruded into smooth and compact strips with the same diameter through a sieve plate of an extruder, sheared, rolled into pellets, baked at 40-50° C. for 3-4 h, sieved to take pellets of 20-30 meshes.

Example 4 Preparation of Health Care Product

Preparation of capsules containing the argininyl fructosy glucose: 100 g of the argininyl fructosy glucose was added with and uniformly mixed with appropriate amount of starch and lactose in a manner of increment by equal quantity, then filled into capsules after passing the inspection, and packaged to obtain the finished product. 800 capsules were prepared, each containing 125 mg of the argininyl fructosy glucose.

Example 5 Preparation of Food

Preparation of tableting candies of the argininyl fructosy glucose: according to the mass percentage, 60% of ginseng powder is mixed with 5% of the argininyl fructosy glucose, 25% of sorbitol, 9% of the microcrystalline cellulose and 1% of magnesium stearate fully and evenly, tableted to obtain finished products, each weighing 0.6 g.

Example 6 Protective Effect of Argininyl Fructosy Glucose (AFG) on Acute Hepatic Failure Caused by Use of Combination of Lipopolysaccharide and D-Galactosamine The experimental animals were male Kunming mice that were weighed 20±5.0 g, provided by SPF Experimental Animal Center of Dalian Medical University, and had a certificate number of CXK2 008-0 002, and had free access to drinking water at a room temperature of 25±3° C.

I. Establishment of Acute Hepatic Failure Model in Mice

Healthy SPF-grade Kunming mice of 20±5.0 g were randomly divided into 5 groups with 6 mice in each group, with the blank group being a group of normal saline+normal saline, the model group being a group of normal saline+ LPS+D-GalN, the low-dose group being a group of 25 mg/kg of AFG+LPS+D-GalN, the medium-dose group being a group of 0 mg/kg of AFG+LPS+D-GalN, and the high dose group being a group of 100 mg/kg of AFG+LPS+ D-GalN.

The AFG, LPS and D-GalN were dissolved in normal saline, with the administration dose of LPS being 40 μg/kg and the administration dose of D-GalN being 700 mg/kg. The mice of the blank group and the model group were given the equivalent dose of normal saline by gavage for three consecutive days before the establishment of the model. The mice of the groups pre-protected with low, medium and high doses of the AFG were given the corresponding doses of the AFG by gavage respectively. Upon the third day of gavage, the mice of the blank group were given the equivalent dose of normal saline by intraperitoneal injection, and the mice of the model group and the groups with low, medium and high doses were given the LPS and the D-GalN by intraperitoneal injection. After 6 hours of modeling, blood and liver tissues were taken. Whole blood was centrifuged (4000 rmp×10 min), and then the supernatant was taken. The liver tissue was washed with normal saline, one-fourth of the large liver lobe was stored in a formalin solution, and the rest of the liver was stored in a refrigerator of −80° C.

II. Determination of Serum Biochemical Indicators

Plasma was taken, and determined with alanine transaminase (GPT) and aspartate transferase (GOT) kits. The experiment followed the instructions of the kits available from Nanjing Jiancheng Bioengineering Institute.

III. Determination of Liver Tissue Biochemical Indicators

The liver tissue homogenate was detected with glutathione (GSH), superoxide dismutase (SOD), malondialdehyde (MDA) and catalase (CAT) kits. The experiment followed the instructions of kits available from Nanjing Jiancheng Bioengineering Institute.

IV. Morphological Observation of Liver Tissue

The in vitro liver tissue was spread on a white paperboard, observed for the appearance of the liver tissue, and photographed.

V. Pathological Observation of Liver Tissue

The liver tissue was soaked in a 10% formalin solution, washed under running water, dehydrated with ethanol solutions of low to high concentrations, xylene solution, embedded with paraffin, sectioned, stained with H&E, and observed under a microscope for the pathological morphology of the liver tissue.

All experimental data were analyzed by a Graphpad Prism 7.0 software. Statistical analysis between the two groups was conducted by a t test. Variance analysis was conducted by Ordinary one-way ANOVA. A Multiple Comparison method was used for conducting pairwise comparison among multiple groups. When the P value was <0.05, it was considered that there was statistical difference among the data of each group.

VI. Determination Results

1. Effects of AFG on AST and ALT in Mice with LPS/ D-GalN-Induced Acute Hepatic Failure Compared with the normal control group, the levels of AST and ALT in the serum of mice of the model group were significantly increased ($P<0.01$), and thus it was inferred that the liver cells were injured or subjected to necrosis. After continuous administration of the AFG for three days, the levels of AST and ALT in the serum of mice of the group with the high dose of the AFG were significantly decreased ($P<0.01$) compared with the model group, indicating that the hepatic failure was relieved. This showed that the AFG could alleviate the LPS/D-GalN-induced acute hepatic failure, and the results were shown in Table 1.

TABLE 1

Effects of AFG on AST and ALT Levels in Mice with LPS/D-GalN-induced Acute Hepatic Failure

| Groups | Dose (mg/kg) | Aspartate transferase (AST) | Alanine transferase (ALT) |
|---|---|---|---|
| Blank group | — | 43.39 ± 3.10 | 6.45 ± 3.14 |
| Model Group | — | 275.08 ± 8.87** | 189.81 ± 6.01**## |
| Group with a low dose of AFG | 25 | 260.52 ± 5.58** | 187.45 ± 3.48**## |
| Group with a medium dose of AFG | 50 | 146.43 ± 0.93* | 116.13 ± 3.37**## |
| Group with a high dose of AFG | 100 | 80.48 ± 5.09* | 71.90 ± 5.97**## |

Note:
compared with the normal control group,
*$P < 0.05$, and
**$P < 0.01$; and compared with the model group,
$P < 0.05$,
$P < 0.01$ 2. Effects of AFG on CAT, GSH, MDA and SOD in Mice with LPS/D-GalN-Induced Acute Hepatic Failure Compared with the normal control group, the levels of CAT, MDA and SOD in the model group were decreased significantly ($P<0.05$), suggesting the accumulation of lipid peroxidation products in the mice and the decrease of antioxidant metabolism level. Compared with the model group, the levels of CAT, MDA and SOD in the groups administrated with medium and high doses of the AFG were increased significantly ($P<0.05$), indicating that the AFG could alleviate lipid peroxidation caused by the LPS/D-GalN to a certain extent and regulate the antioxidant metabolism level in the mice. The results were shown in Table 2.

TABLE 2

Effects of AFG on CAT, GSH, MDA and SOD Levels in Mice with LPS/D-GalN-Induced Acute Hepatic Failure

| Groups | Dose (mg/kg) | Catalase (CAT) | Glutathione (GSH) | Malondialdehyde (MDA) | Superoxide dismutase (SOD) |
|---|---|---|---|---|---|
| Blank group | — | 42.67 ± 11.39 | 45.51 ± 4.83 | 80.24 ± 12.88 | 26.12 ± 1.94 |
| Model Group | — | 17.84 ± 0.82* | 27.04 ± 2.16 | 135.80 ± 11.29** | 9.10 ± 0.98** |

TABLE 2-continued

Effects of AFG on CAT, GSH, MDA and SOD Levels in
Mice with LPS/D-GalN-Induced Acute Hepatic Failure

| Groups | Dose (mg/kg) | Catalase (CAT) | Glutathione (GSH) | Malondialdehyde (MDA) | Superoxide dismutase (SOD) |
|---|---|---|---|---|---|
| Group with a low dose of AFG | 25 | 34.01 ± 2.75 | 51.91 ± 3.29 | 133.37 ± 5.38** | 11.48 ± 1.77** |
| Group with a medium dose of AFG | 50 | 51.66 ± 6.19## | 67.94 ± 3.58 | 104.00 ± 3.13# | 20.98 ± 3.72## |
| Group with a high dose of AFG | 100 | 61.44 ± 8.96## | 136.00 ± 6.90**## | 94.44 ± 6.87## | 26.54 ± 2.93## |

Note:
compared with the normal control group,
*$P < 0.05$, and
**$P < 0.01$; and compared with the model group,
$P < 0.05$,
$P < 0.01$ 3. Morphological Appearance of Liver Tissue After the mice were sacrificed by cervical dislocation, the liver tissues were taken, and the in vitro liver tissues were observed. From the appearance and morphology, the liver of the mice in the model group wholly showed a black-red morphology, and the color was significantly different compared with the normal control group. After the AFG was given for protection, the appearance of the liver gradually tended to be of a normal state with the increase of the protection dose, especially in the group protected with the high dose, the protection effect was obvious.

4. H&E Staining of Liver Tissue

The liver tissues of mice were sectioned and made into H&E stained sections for observation. The results showed that: compared with the normal control group, the liver cells in the model group showed massive coagulation necrosis, formation of acidophilic bodies, infiltration of glial cells, and cellular karyorrhexis. Compared with the model group, in the group with the medium dose of the AFG, cellular necrosis was significantly improved, the number of cell nucleus was significantly increased, and the cell structure was repaired; in the group with the high dose of the AFG, the cells had relatively complete structures, arranged regularly, and thus the effect of the AFG was more obvious, figures were omitted.

5. TUNEL Staining of Liver Tissues

In order to further confirm the protective effect of the AFG on the mice with the LPS/D-GalN-induced acute hepatic failure, the liver tissues were subjected to TUNEL staining. The results showed that: the liver cells of the mice in the normal control group had intact structures and showed no apoptosis after subjected to the TUNEL staining; in the model group a large number of stained positive cells appeared, suggesting that the LPS/D-GalN could induce liver cell apoptosis; and compared with the model group, in the treatment group administrated with the AFG, the number of apoptotic cells was significantly reduced and the apoptosis situation was improved.

In view of the above, the AFG in the range from 50 mg/kg to 100 mg/kg can significantly improve the acute hepatic failure caused by the combination of the LPS and the D-GalN, is a promising liver protective agent that mainly protects the liver by improving the level of acute oxidative stress and apoptosis.

The use of the AFG of the present invention in the preparation of the drug for preventing the acute hepatic failure has been described above according to the aforementioned implementation method, but the present invention is not limited to the aforementioned implementation method, and the present invention can be implemented in various ways without departing from the topic thereof. In addition to the aforementioned implementation method, other equivalent technical solutions should also be within the claimed scope of the present invention, and will not be described here.

What is claimed is:

1. A method of treating an acute hepatic failure disease, comprising administering to a subject in need thereof a therapeutically effective amount of purified or chemically synthesized argininyl fructosy glucose of the following formula:

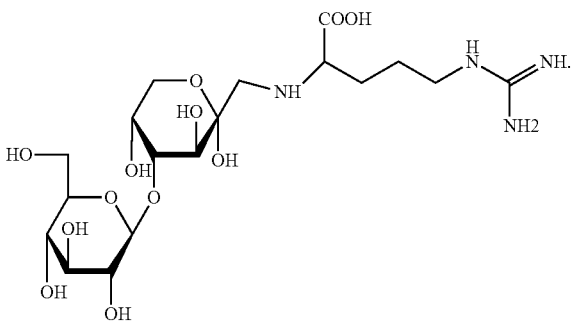

2. The method of claim 1 wherein the purified or chemically synthesized argininyl fructosy glucose has a purity of no less than 80%.

3. The method of claim 1 wherein the purified or chemically synthesized argininyl fructosy glucose has a purity of greater than 98.5%.

4. The method of claim 1 wherein the purified or chemically synthesized argininyl fructosy glucose has a purity of 80%-99.99%.

5. The method of claim 1 wherein the acute hepatic failure disease is an oxidative stress injury caused by use of a combination of lipopolysaccharide (LPS) and D-galactosamine (D-GalN).

6. The method of claim 1 wherein the treating comprises protecting liver cells from injuries and reducing apoptosis caused by LPS/D-GalN.

7. The method of claim 1 comprising formulating the purified or chemically synthesized argininyl fructosy glucose in a composition additionally comprising an auxiliary ingredient or an additive ingredient prior to administering.

8. The method of claim 7 wherein the composition comprises the purified or chemically synthesized argininyl fructosy glucose as a sole active ingredient.

9. The method of claim 7 wherein the composition is in a dosage form selected from the group consisting of powder, tablets, pills, granules, capsules, solutions, injections, powder injections, and patches.

10. The method of claim 9 wherein the composition is in a dosage form selected from the group consisting of tablets, pills, granules, capsules, injections, powder injections, and patches.

11. The method of claim 1 wherein the administering comprises administering the purified or chemically synthesized argininyl fructosy glucose to the subject in an amount of 50 mg/kg to 100 mg/kg.

\* \* \* \* \*